United States Patent [19]

Nogami et al.

[11] Patent Number: 5,100,557
[45] Date of Patent: Mar. 31, 1992

[54] LIQUID CHROMATOGRAPHY SYSTEM AND METHOD FOR SEPARATION OF PRE-SEPARATED COMPONENTS

[75] Inventors: Taro Nogami; Hironori Kaji, both of Katsuta; Kaoru Hagiya, Hitachi; Katsuo Tsukada, Ibaraki; Yoshinori Takata, Chiba, all of Japan

[73] Assignee: Hitachi, Ltd., Tokyo, Japan

[21] Appl. No.: 443,149

[22] Filed: Nov. 30, 1989

[30] Foreign Application Priority Data

Dec. 9, 1988 [JP] Japan .................. 63-310024

[51] Int. Cl.$^5$ .............................. B01D 15/08
[52] U.S. Cl. ..................... 210/656; 210/198.2; 422/70; 73/61.1 C
[58] Field of Search ............. 210/656, 659, 198.2; 55/67, 386; 422/70; 73/61.1 C

[56] References Cited

U.S. PATENT DOCUMENTS

| | | | |
|---|---|---|---|
| 4,724,081 | 2/1988 | Kawahara et al. | 210/198.2 |
| 4,806,250 | 2/1989 | Takata et al. | 210/198.2 |
| 4,849,110 | 7/1989 | Takata et al. | 210/656 |
| 4,859,342 | 8/1989 | Shirasawa et al. | 210/659 |

FOREIGN PATENT DOCUMENTS 87133505 7/1987 Fed. Rep. of Germany.
3925460 8/1990 Fed. Rep. of Germany.
62-75261 7/1987 Japan.

OTHER PUBLICATIONS

Kirkland, "Introduction to Modern Liquid Chromatography," John Wiley & Sons, Inc., New York, 1979, pp. 519–520.

Primary Examiner—Robert A. Dawson
Assistant Examiner—Sun Uk Kim
Attorney, Agent, or Firm—Fay, Sharpe, Beall, Fagan, Minnich & McKee

[57] ABSTRACT

A liquid chromatography system and a method of utilizing the same, comprising a plurality of separated-component vessels for collecting components eluted in a separation column, a flowing system conduit for component extraction through which the components separated in the separation column are individually delivered to the separated-component vessels. The system further comprises a flowing system conduit for sample introduction through which any of the separated components collected in the plurality of separated-component vessels is selectively drawn from its vessel and introduced to the upstream side of the separation column. The present invention allows a plurality of components in a sample of a mixture to be individual collected, and also allows any of the collected components to be re-separated selectively and automatically.

18 Claims, 8 Drawing Sheets

LIQUID CHROMATOGRAPHY SYSTEM AND METHOD FOR SEPARATION OF PRE-SEPARATED COMPONENTS

FIELD OF THE INVENTION AND RELATIVE APPLICATION

The present invention relates to a liquid chromatography system and, more particularly, to a liquid chromatography system suitable for individually collecting components in a sample of a mixture.

In a conventional liquid chromatography system for separating a component from a sample containing a mixture of a plurality of components, as disclosed in Japanese Patent Unexamined Publication No. 62-75261, when some chromatographic peaks of sample components eluted from a column were detected to be overlapped due to insufficient separation of a certain component, the sample components which had originated these unfavorable peaks were retained within a sample loop for a while, and then, they were repeatedly passed through the column for re-separation by shifting a passway of eluent within a six-way valve so that the required sample component was collected into a fraction collector.

SUMMARY OF THE INVENTION

In the conventional system described above, if the separation of the required sample component was not satisfactorily completed, a sample consisting of the required sample component and unrequisite sample components which belonged to a certain component region of chromatography was repeatedly passed through the column so as to separate the required sample component. Therefore, when a plurality of sample components was required to be collected, it was a problem that, while such separation of one required sample component was repeated, other required sample components could not be collected.

One object of the present invention is to individually collect a plurality of components in a sample of a mixture, and also to re-separate any of the collected components selectively and automatically.

In order to achieve this object, a liquid chromatography system of the present invention supplies eluent to a separation column, and a sample of a mixture to be separated is introduced to a flow of this eluent, so that components separated from this sample are individually collected. The invention comprises a plurality of separated-component vessels for collecting the components eluted in the separation column, a flowing system conduit for component extraction through which the components separated in the separation column are individually delivered to the separated-component vessels, and a flowing system conduit for sample introduction through which any of the separated components collected in the plurality of separated-component vessels is selectively drawn from its vessel and introduced to the upstream side of the separation column. The component extraction flowing system conduit and the sample introduction flowing system conduit each includes a common conduit section at certain regions of the respective conduits, with a mechanism for cleaning this common conduit section being further provided.

In addition, the liquid chromatography system of the present invention further includes a sample injection chamber located between an eluent supplying pump and the separation column, a nozzle inserted selectively to the separated-component vessels, and a device operating this nozzle in such a manner that any of the separated components collected in the plurality of separated-component vessels is selectively drawn through the nozzle from its vessel and introduced into the sample injection chamber. A connecting member is also provided for connecting the nozzle and the conduit at the downstream side of the separation column. For this connecting member, it is desirable to use a valve by which the conduit at the downstream side of the separation column can be disconnected from the nozzle and connected with a drain.

The liquid chromatography system of the present invention may alternatively include a plurality of channels associated with the respective separated-component vessels for delivering the components eluted in the separation column therethrough, and a device by which any of the channels is selected to introduce the component collected in the associated separated-component vessel to the flow of the eluent. A sample introducing valve device is located between an eluent supplying pump and the separation column, with a port being provided on the sample introducing valve device so that the sample can be injected therethrough from the outside. The above-mentioned channels are provided with opening and closing valves for selectively opening/closing the respective channels. A connecting member is further provided to selectively connect the downstream side of the separation column with a flowing system conduit for component extraction or with a drain.

A method of utilizing the liquid chromatography system of the present invention is characterized by comprising the steps of introducing a sample to the separation column; collecting components separated in the separation column via the common conduit section into a plurality of separated-component vessels; cleaning the common conduit section; and selectively drawing any of the components from its separated-component vessel through the cleaned common conduit section and introducing this component to the separation column.

According to the liquid chromatography system of the present invention, a single component or a plurality of components in a sample which have been separated in the separation column are collected into the respective separated-component vessels provided independent from the flowing system by the operation of the single nozzle or the opening and closing valves provided on the channels for delivering the components eluted in the separation column therethrough. If any of these collected components is not satisfactorily separated, it can be re-injected into the separation column, re-separated in it, and re-collected as the component of high purity. This effect can be obtained in such a manner that, by suction operation of a syringe, a component in the separated-component vessel is drawn in through the common conduit section, i.e., a certain section which the component extraction flowing system conduit and the sample introduction flowing system conduit have in common, and then, by injection operation of the syringe, the component is injected through the sample introduction flowing system conduit into the separation column.

BRIEF DESCRIPTION OF THE DRAWINGS

The above and further objects, features, and advantages of the present invention will be more apparent from the following description of preferred embodiments of the present invention with reference to the drawings in which.

DESCRIPTION OF PREFERRED EMBODIMENTS

Preferred embodiments of a liquid chromatography system according to the present invention will be described below by referring to the attached drawings.

Figure 1:
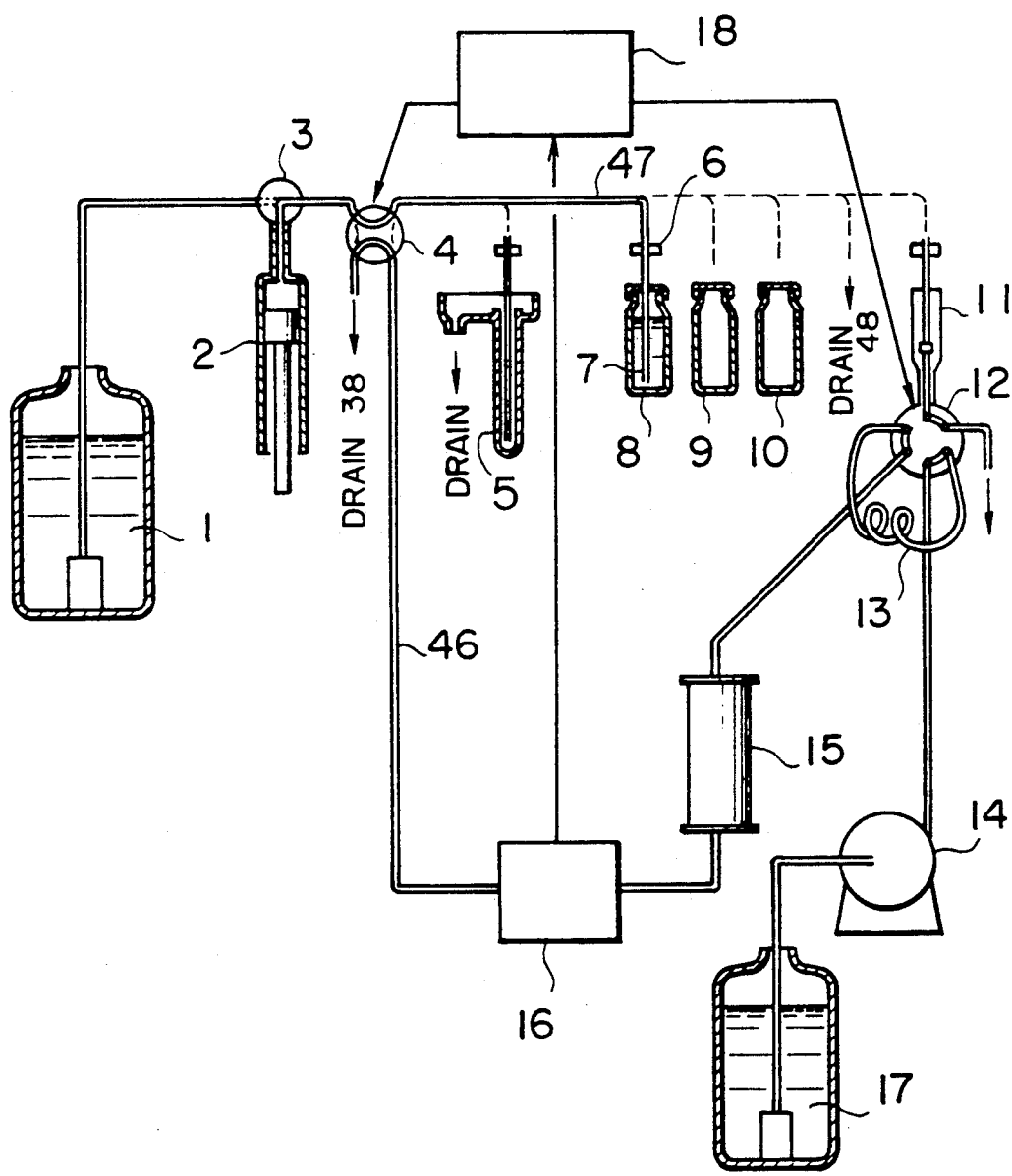
FIG. 1 is a diagrammatically explanatory view showing a first embodiment according to the present invention.

A first embodiment of the present invention will now be explained with reference to FIG. 1. From a sample vessel 8 containing a sample, the sample is drawn in through a nozzle 7 by suction operation of a syringe 2 to fill up a flowing system conduit 47 for sample introduction. After that, the nozzle 7 is transferred to a sample injection chamber 11, where the sample is introduced into a metering pipe 13 connected with a six-way valve 12 serving as a sample introducing valve device by injection operation of the syringe 2. At this time, the six-way valve is so turned that eluent 17 will not flow into the metering pipe 13. During the suction and injection of the sample, a four-way valve 4 serving as a connecting member of the nozzle 7 with a flowing system conduit 46 for component extraction which connects the nozzle 7 with the downstream side of a separation column 15 and a three-way valve connected with the syringe 2, detergent 1, and the four-way valve 4 have such passways as shown in FIG. 1. Next, by shifting the six-way valve 12, the sample in the metering pipe 13 is introduced to a flow of the eluent supplied by an eluent supplying pump 14 to enter the separation column 15. A component separated from the mixture of the sample and the eluent within the separation column 15 is detected by a detector 16, and a signal of the detection is transmitted to a control circuit 18. On the basis of information of this signal, the control circuit 18 operates various valves and driving devices of the nozzle 7. While only the eluent is flowing, it is usually discharged through a drain 38 of the four-way valve, but when the four-way valve is turned, the eluent 17 is directed toward the nozzle 7. In this case, until the eluted component from the separation column 15 reaches the nozzle 7, the eluent 17 is discharged through the nozzle 7 to a drain 48, but when the eluted component is detected by the detector, this component is collected flowing through the nozzle 7 into a primary separated-component vessel 9 among a plurality of separated-component vessles. Then, the nozzle 7 is transferred to a cleaning receptacle 5, and the detergent is drawn into the syringe 2 by shifting the three-way valve 3. By turning the three-way valve 3 again, the nozzle 7 and a common conduit section of the sample introduction flowing system conduit 47 and component extraction flowing system conduit 46 which are both connected with the nozzle 7 are cleaned with the drawn detergent 1 flowing through the common conduit section and the nozzle. If the separation of the component is not satisfactorily completed, the nozzle 7 is again transferred to the primary separated-component vessel 9, and the collected component is drawn in by the suction operation of the syringe 2, and is introduced through the sample injection chamber 11 to the separation column 15 to carry out re-separation. After repeating the same operation as described above, the component separated for the second time is collected into a secondary separated-component vessel 10. Although the primary collection and the secondary collection are performed each once in the case explained heretofore, the primary collection, for example, can be repeated as many times as a plurality of components before starting the secondary collection. Further, the operation will be concretely described below.

Figure 2:
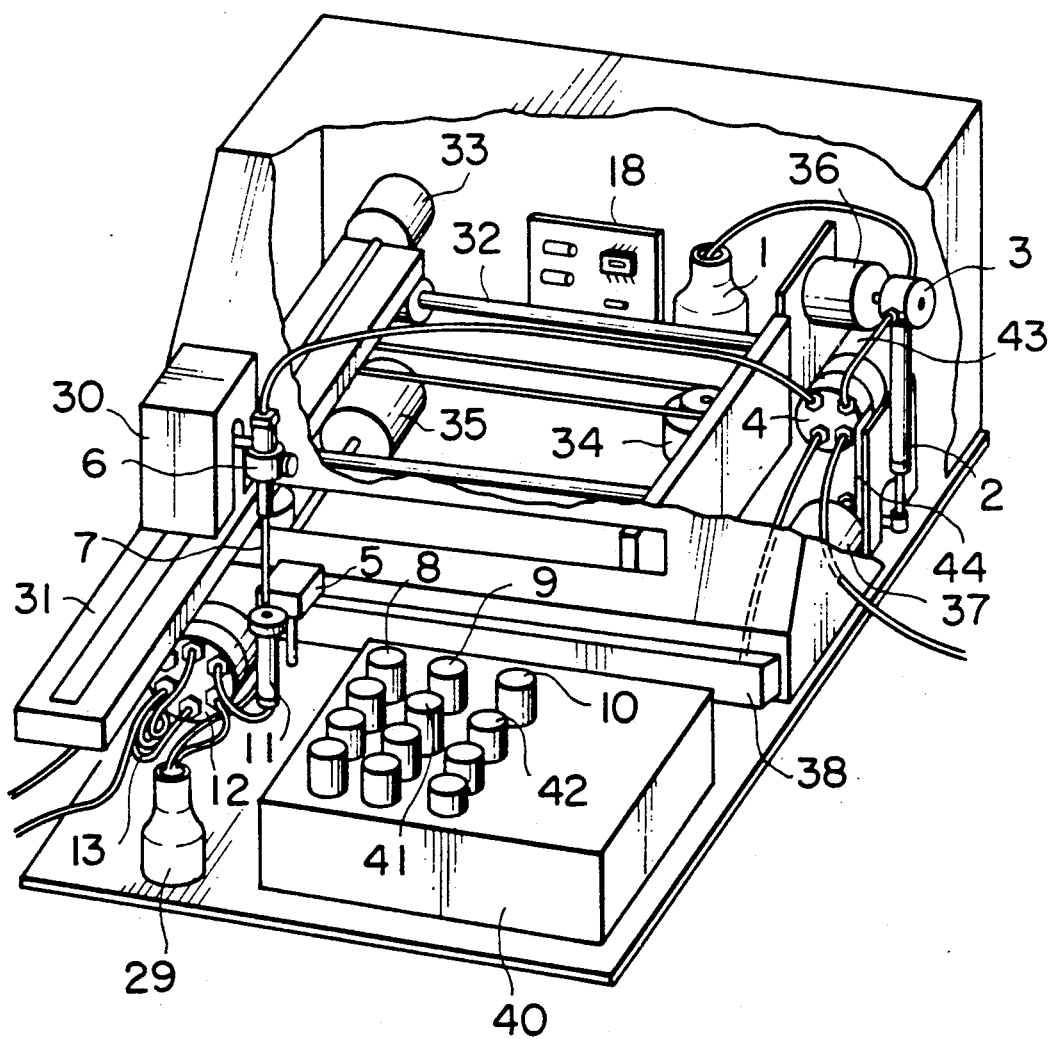
FIG. 2 is a perspective explanatory view, partially broken away, showing operational systems in a main portion of the first embodiment.

Operational systems in a main portion of the embodiment shown in FIG. 1 are illustrated in FIG. 2. The same members as shown in FIG. 1 are denoted by the same reference numerals. The nozzle 7 is moved up and down by a vertical or up-down driving mechanism 30, as viewed in FIG. 2. The nozzle 7 is moved down to the lowermost position a) to draw a sample or a component collected for the first time from the vessel, b) to be inserted to the sample injection chamber 11 for introducing the sample to the metering pipe 13, c) to be inserted to the cleaning receptacle 5, and d) to meet requirements, for example, to draw diluent from a vessel containing the diluent if assuming that the collected component is too little to be drawn from the component vessel. An operational system including the nozzle 7, an arm 6, and the up-down driving mechanism 30 is moved forwardly and backwardly by a longitudinal or foreback driving mechanism 31 actuated by a pulse motor 33. The fore-back driving mechanism integrally incorporated with the nozzle 7, the arm 6, and the up-down driving mechanism 30 is moved leftwardly and rightwardly by a lateral or left-right driving mechanism 32 actuated by a pulse motor 34. The six-way valve 12, the four-way valve 4, and the three-way valve 3 are independently operated by the respective pulse motors 35, 43, and 36. Also, the suction and injection operations of the syringe 2 are effected by a syringe driving mechanism 44 actuated by a pulse motor 37. The pulse motors are controlled by the control circuit 18, respectively. The sample vessel 8, the primary separated-component vessel 9, and the secondary separated-component vessel 10 are arrayed to set in a vessel receiving rack 40, where collection of the component in the sample is performed, as explained with reference to FIG. 1. When the sample contains two components to be collected, they are respectively collected into the primary separated-component vessel 9 for the first-kind component and a primary separated-component vessel 41 for the second-kind component during the primary collection, and then, the components are respectively collected into the secondary separated-component vessel 10 for the first-kind component and a secondary separated-component vessel 42 for the second-kind component during the secondary collection. When the sample contains more than two components to be collected, more than two primary separated-component vessels and more than two secondary separated-component vessels are prepared for performing the same collection operations.

In this system, it is necessary to discharge components which are not required to be collected, the eluent, the detergent after cleaning the nozzle 7 and the common conduit section, and the like, and such discharged liquid is collected directly through the nozzle 7 or via the drain 38 into a waste liquid bottle.

In addition, although not shown in FIG. 2, the eluent supplying pump 14, the separation column 15, and the detector 16 are installed. The eluent supplying pump 14 and the separation column 15 are communicated with the six-way valve 12, and the detector 16 is communicated with the four-way valve 4.

Figure 5:
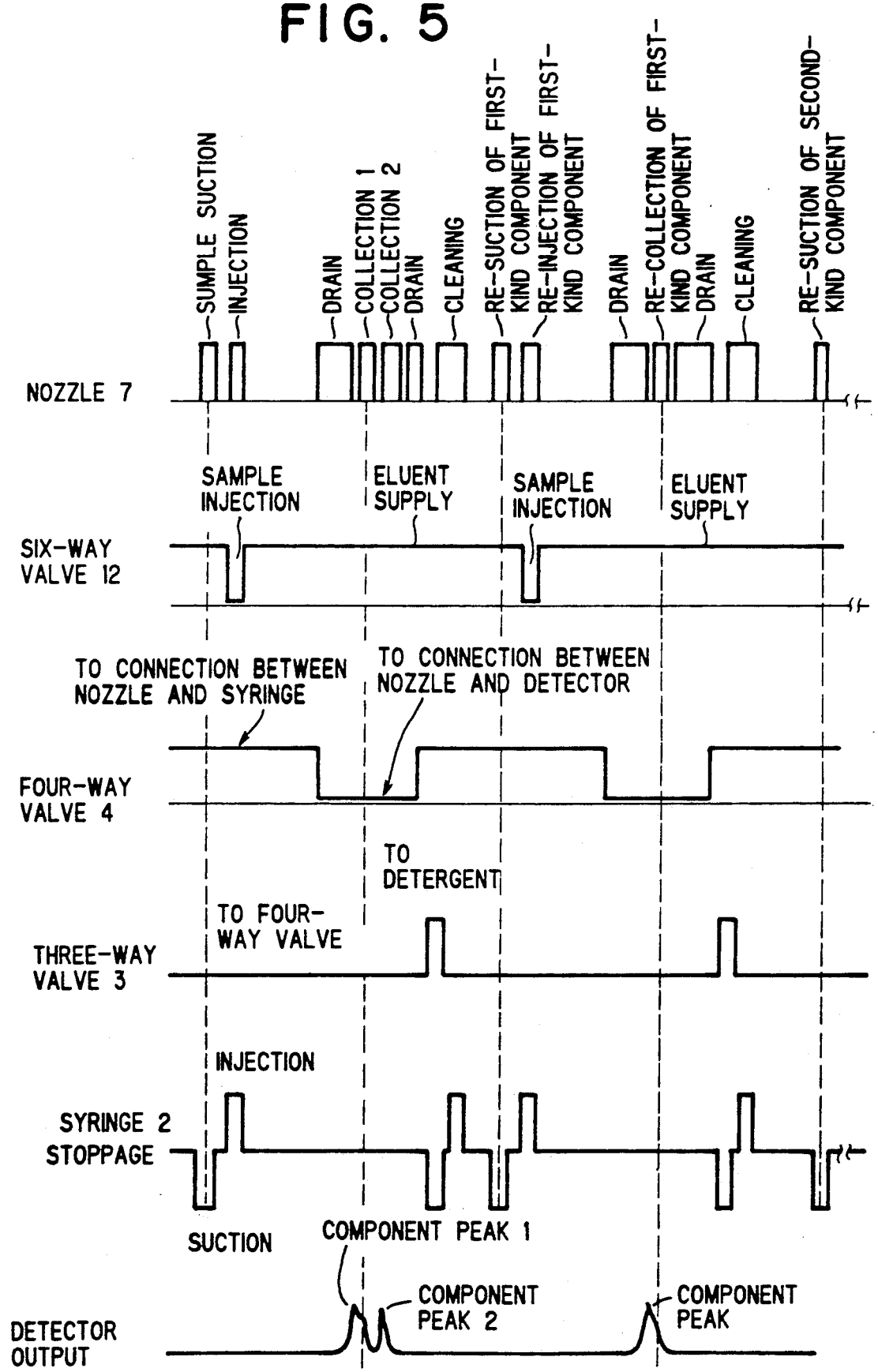
FIG. 5 is a timing chart showing the operations of the system according to the first embodiment.

FIG. 5 illustrates a timing chart for explaining the operation of each member in the embodiment shown in FIG. 1 with reference to the operation of the mechanisms.

When the nozzle 7 is held down in the sample vessel 8, the three-way valve 3 is so arranged that the pass way is connected from the syringe 2 to the four-way valve 4. It is this arrangement that is shown in FIG. 1. In this condition, when the suction operation of the syringe 2 is done, the sample in the sample vessel 8 is drawn through the nozzle 7 into the sample introduction flowing system conduit 46. In the meantime, the six-way valve 12 has such connecting arrangement as shown in FIG. 1, whereby the eluent is being supplied to the separation column 15 by the pump 14.

Figure 7:
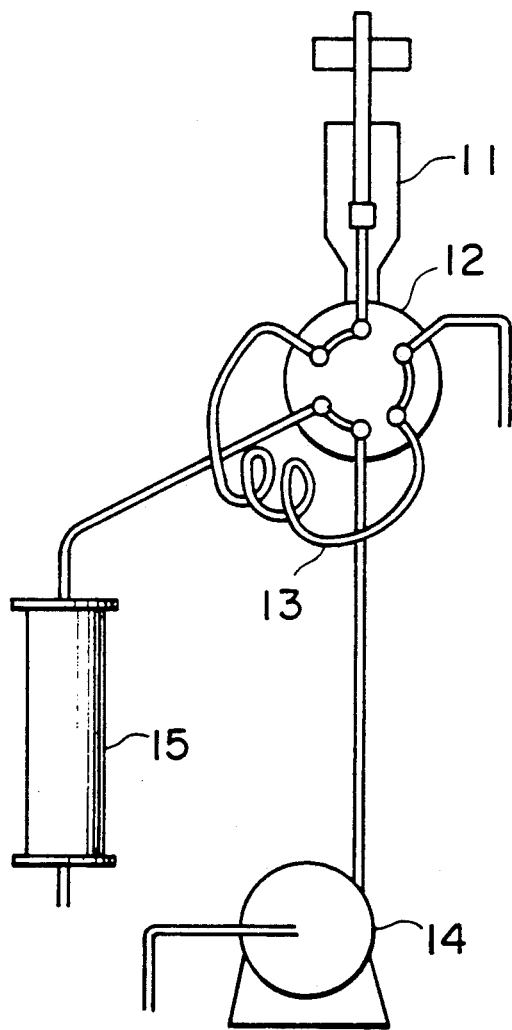
FIGS. 7 and 8 are partial schematic views showing portions of the system of the embodiment shown in FIG. 5, which are in certain conditions for explaining them more particularly.

As illustrated in the timing chart of FIG. 5, when the nozzle 7 is set for injection, i.e., when the nozzle 7 is inserted to the sample injection chamber 11, the six-way valve 12 is rotated to a position for the sample injection. The six-way valve 12 at this position for the sample injection has such connecting arrangement as shown in FIG. 7. The injected sample is contained within the metering pipe 13. When the six-way valve 12 returns to the former position for the eluent supply to have the connecting arrangement shown in FIG. 1, the sample in the metering pipe 13 is introduced to the separation column 15.

Figure 8:
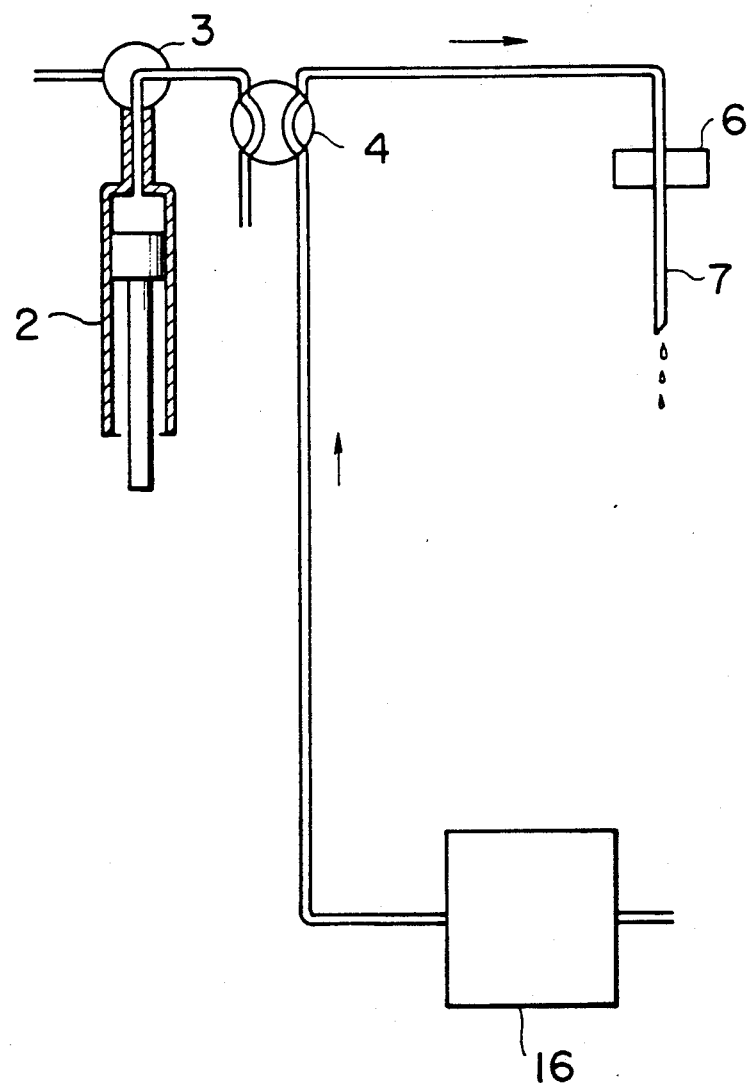

The time chart of FIG. 5 shows that during the suction and injection of the sample, the four-way valve 4 is always arranged to have the nozzle 7 and the syringe 2 communicating with each other, as described above. Therefore, after passing through the separation column 15 and the detector 16, the eluent is discharged into the drain 48. When the four-way valve 4 is changed from this position to the position of having the nozzle 7 and the detector 16 communicating with each other, the eluent which has passed through the separation column 15 and the detector 16 is delivered to the nozzle 7 and flows out of it. The four-way valve 4 of this connecting arrangement is shown in FIG. 8. In this condition, the eluent is first discharged into the drain 38. Taking into consideration a slight time lag of flow conveyance of the component from the detector 16 to the nozzle 7, within a certain period of time after increase of a component peak 1 of the first-kind component is detected by the detector 16, the nozzle 7 is transferred to the separated-component vessel 9 for collecting the first-kind component. Similarly, within a certain period of time after decrease of the component peak 1 is detected by the detector 16, the nozzle 7 is moved away from the separated-component vessel 9, the collection of the component referred to as the collection 1 in FIG. 5 is completed. Succeedingly, in accordance with information of a component peak 2 of the second-kind component from the detector 16, the collection 2 is performed using not the separated-component vessel for the collection 1 but a different component vessel. Unless more component peaks for collections are detected, the nozzle 7 is transferred to the drain 48.

Next, the four-way valve 4 returns to the former position to have the nozzle 7 and the syringe 2 communicating with each other, and the eluent from the detector 16 is discharged through the four-way valve 4 into the drain 38. At the same time, the passway of the three-way valve 3 is open for the detergent to pass therethrough, and simultaneously, the detergent 1 is drawn into the syringe 2 by the suction operation. After that, the three-way valve 3 is so turned that the nozzle 7 and the three-way valve 3 are communicated via the four-way valve 4, and the injection operation of the syringe 2 is initiated. During this operation, the nozzle 7 is held within the cleaning receptacle 5, where the nozzle 7 and the common conduit section connected thereto are cleaned with the detergent 1 delivered from the nozzle 7.

If any of the components collected for the first time has insufficient purity which requires improvement, the secondary collection of this component is succeedingly carried out. The sequence of the operations is substantially the same as the case explained above so that the description may be omitted. However, because the component which has already been collected once is re-separated, only one component peak is detected unless a great amount of impurities are observed in the sample. An example of this is shown as a re-collection of the first-kind component in FIG. 5. After re-separation and re-collection of any of the collected components are completed to meet requirements, a new sample is subjected to a next collection in the sequence described heretofore.

Figure 3:
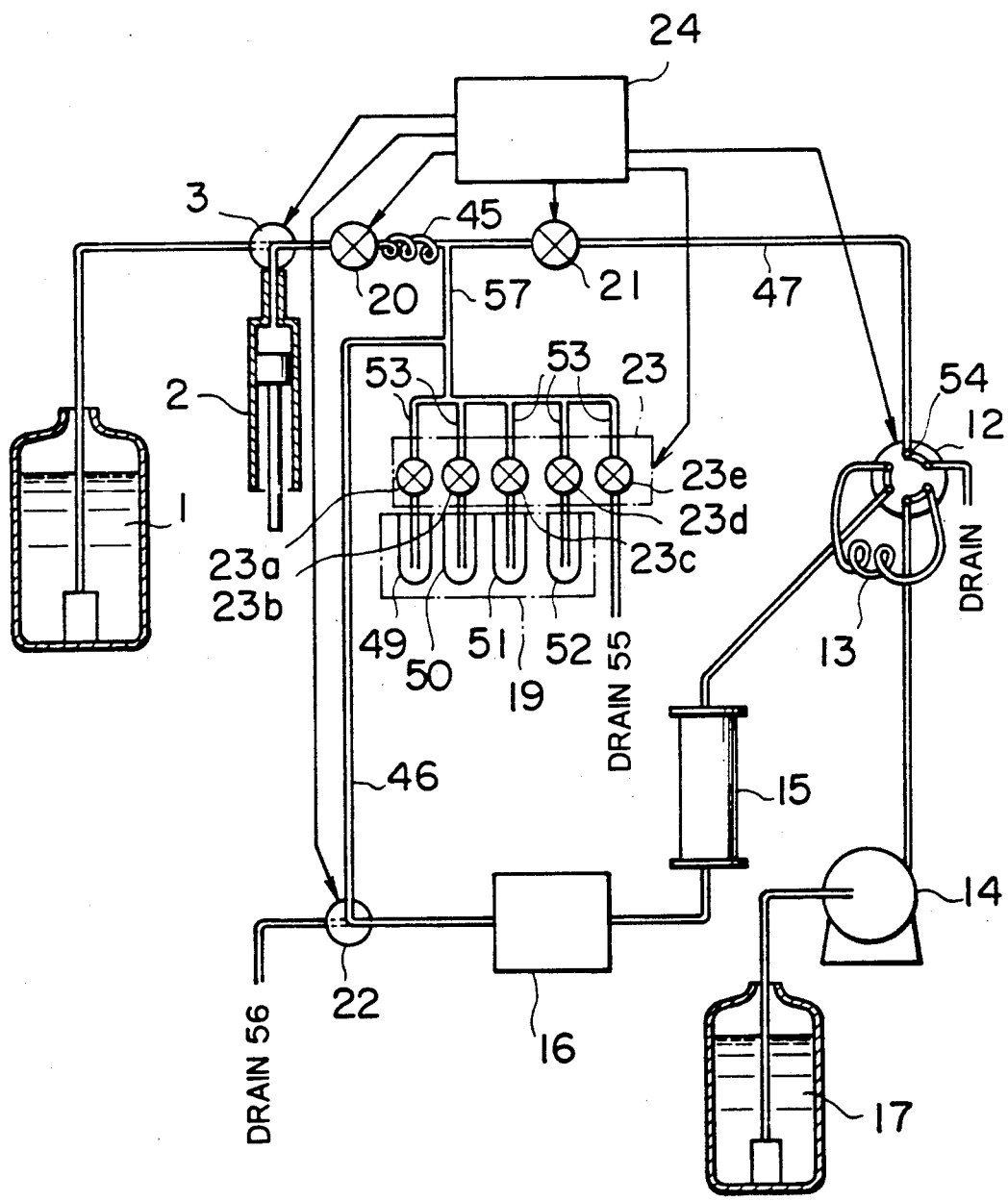
FIG. 3 is a diagrammatically explanatory view showing a second embodiment according to the present invention.

FIG. 3 is an explanatory view of a second embodiment according to the present invention showing structure of a liquid chromatography system. A sample vessel 49 and a plurality of sets of separated-component vessels 50 to 52 are provided in a vessel receiving rack 19. These vessels are respectively provided with a plurality of channels 53 which are connected to the component extraction flowing system conduit 46, and opening and closing valves 23a to 23e are provided on the channels 53. The sample introducing valve device 12 including a sample injection port 54 connected to the sample introduction flowing system conduit 47 is installed on the conduit between the eluent supplying pump 14 and the separation column 15. In addition, a three-way valve 22 is arranged to connect the downstream side of the detector 16 and the component extraction flowing system conduit 46.

Figure 6:
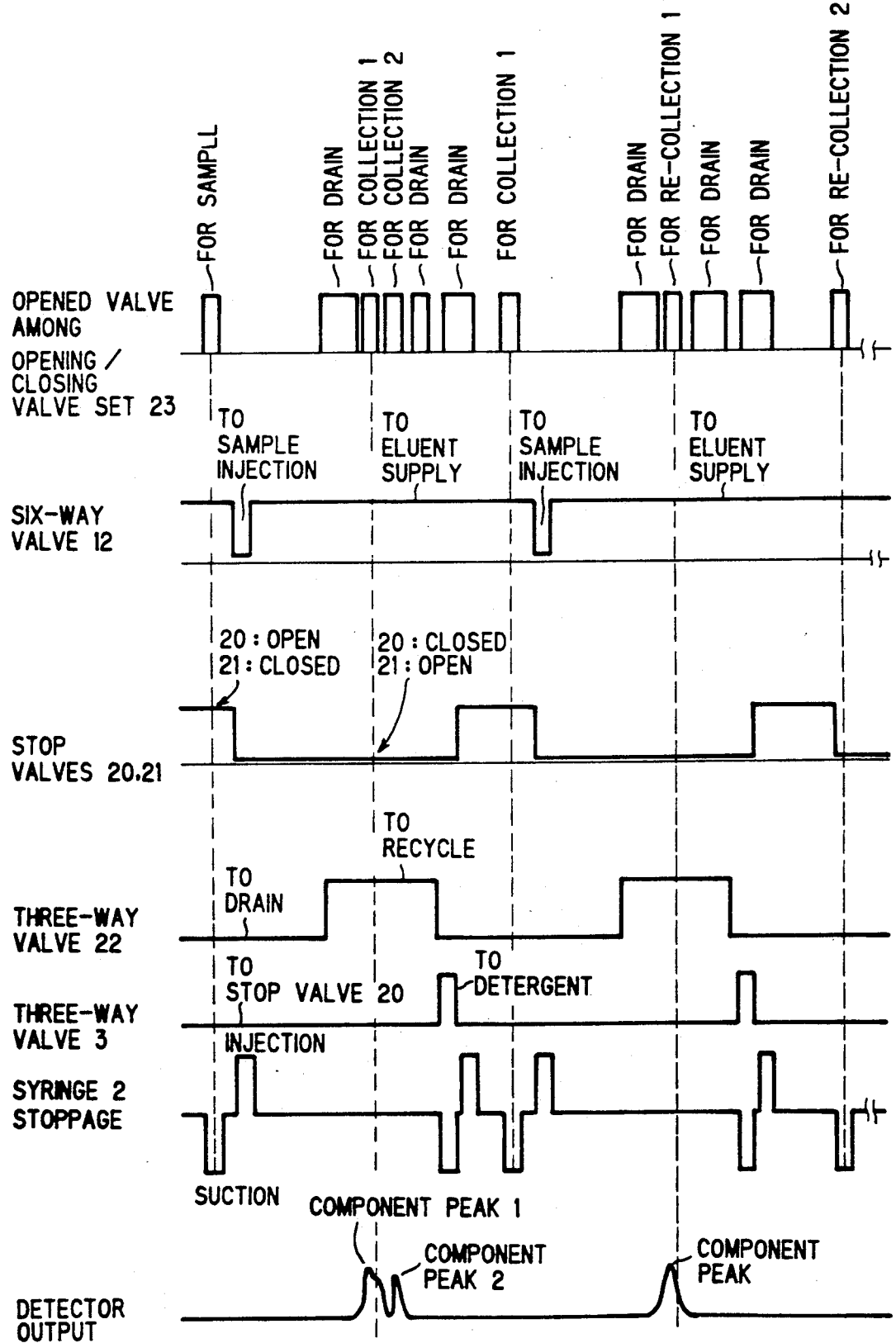
FIG. 6 is a timing chart showing the operations of the system according to the second embodiment.

The operation will be hereinafter explained in detail with reference to FIG. 3 showing the second embodiment of the present invention and FIG. 6 showing a timing chart of the second embodiment.

First, the switch valve 23a provided on the channel inserted to the sample vessel 49 is made open. At this moment, a stop valve 21 is closed, and a stop valve 20 is open. The valve 22 for a drain is open to connect the conduit from the detector 16 to the drain 56. In this condition, when the suction operation of the syringe is done, a sample is drawn from the sample vessel to fill up a sample holding section 45. When the stop valve 20 is made closed, and the stop valve 21 is made open, the injection operation of the syringe 2 is effected. At this moment, the six-way valve 12 is rotated to the position for the sample introduction, and the sample in the sample holding section 45 is introduced through the sample injection port 54 provided on the six-way valve 12 into the metering pipe 13. After that, when the six-way valve 12 returns to the former position for the eluent supply, the sample is delivered to the separation column 15 by the eluent supplying pump 14.

When the three-way valve 22 is operated in such a manner that the downstream side of the detector 16 is communicated with the component extraction flowing system conduit 46, the liquid supplied through the detector 16 is moved from the separation column 15 toward the separated-component vessels 50 to 52. The opening and closing valve 23e for the drain 55 is open at the first stage, but when the component peak is detected by the detector 16, the opening and closing valve 23b associated with the separated-component vessel 50 for collecting the first-kind component is made open, and the first-kind component is collected. Similarly, when the component peak 2 is detected, the opening and closing valve 23c associated with the separated-component vessel 51 for collecting the second-kind component is made open, and the second-kind component is collected. After the collections of the components have been completed, the opening and closing valve for the drain 55 is made open again, and the eluent 17 is drained.

After that, when the three-way valve 22 is so arranged that the drain 56 is communicated with the downstream side of the detector 16, the eluent 17 from the detector 16 is discharged from the drain 56. When the three-way valve 3 connected to the syringe 2 has the passway communicated with the detergent 1, the detergent 1 is drawn into the syringe 2 by the suction operation. When the passway of the three-way valve 3 is turned again, the stop valve 20 is made open, and the stop valve 21 is made closed, so that the sample holding section 45 and a common conduit section 57 of the sample introduction flowing system conduit 47 and component extraction flowing system conduit 46 are cleaned by the injection operation of the syringe 2.

For example, if any of the collected components requires further separation, re-separation and re-collection can be optionally performed by the operations similar to the above-described sequence. This is the same procedure of the embodiment shown in FIG. 1, and accordingly, the detailed description of the operations will be omitted.

An advantageous effect of this embodiment is that it can be operated not only in the above-stated ordinary mode, but also in such a mode that when one component is to be collected, the separated component is not collected in a vessel before re-separation but recycled as it is.

Figure 4:
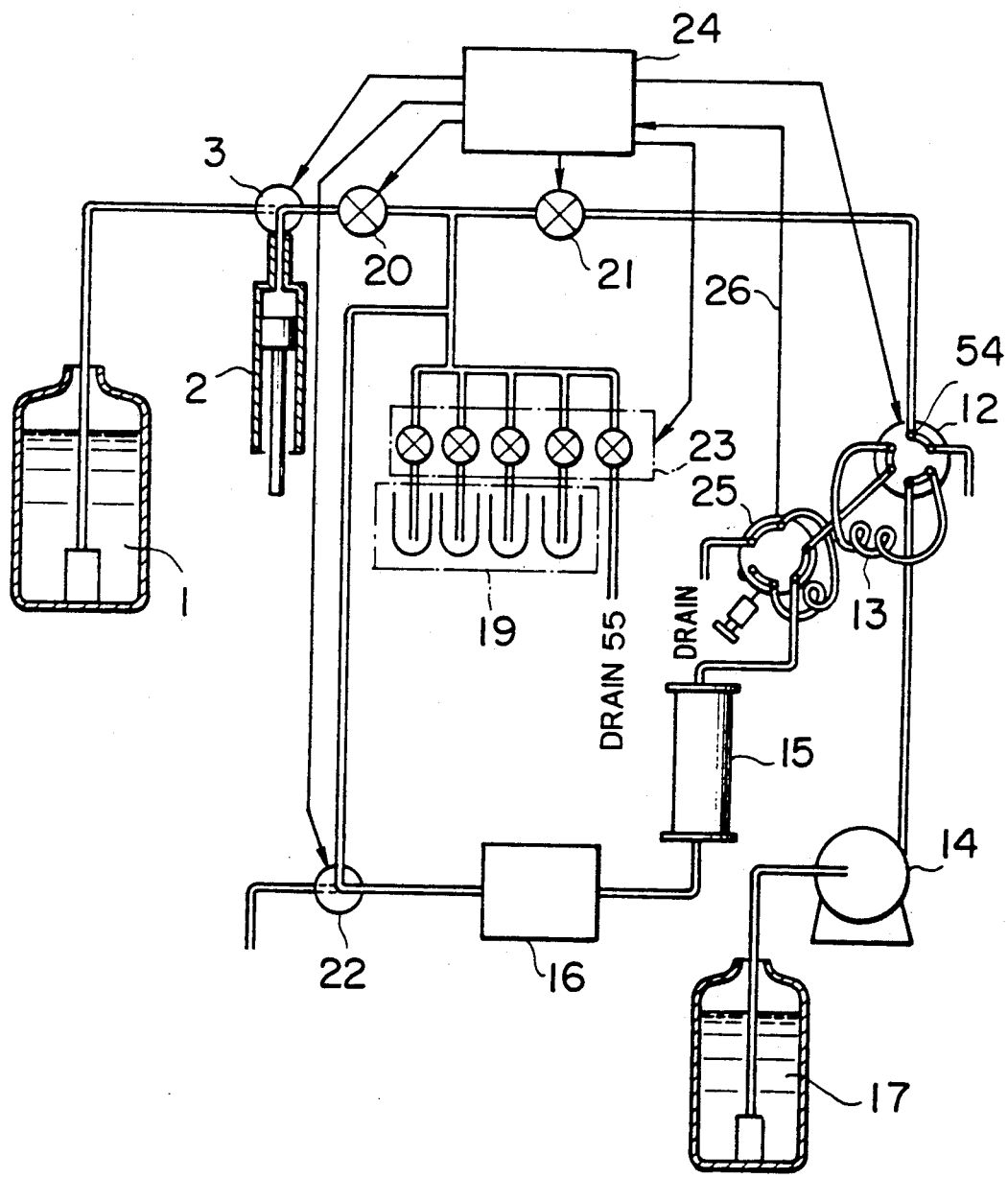
FIG. 4 is a diagrammatically explanatory view showing a modified example of the second embodiment.

Although sampling for the primary collection and sampling for re-separation of the collected sample are carried out using the vessels provided in the vessel receiving rack in the above embodiments, FIG. 4 shows an alternative in which sampling for the primary collection is done by an additionally provided member for sampling, i.e., an injection valve 25, and sampling for re-separation of the component alone is done in the same manner as the second embodiment shown in FIG. 3. It is intended for an experimental collection where a certain sample is manually injected, or for a continuous collection of samples of extremely many kinds. In place of the injection valve, an auto-sampler can be employed.

The present invention, which has the above-stated structure, takes such effects as explained below.

Because a plurality of separated-component vessels are provided independent from the flowing system, and because this flowing system is divided into the component extraction flowing system conduit and the sample introduction flowing system conduit, a single component or a plurality of components in a sample or each of a large number of samples can be individually collected, and besides, any of the components which have been collected once can be optionally introduced to the separation column repeatedly, if necessary.

Further because the component extraction flowing system conduit and the sample introduction flowing system conduit are in conjunction with each other at the common conduit section, suction and injection of the sample or the collected component can be performed by the single flowing system, thereby simplifying the arrangement of the sample introduction.

In addition, the sample or the collected component can be drawn or injected through the single nozzle, and as a result, the arrangement of the sample introduction can be simplified to accomplish the cost reduction.

Alternatively, a plurality of separated-component vessels are respectively provided with a plurality of channels, on which the respective opening and closing valves are mounted, so that the liquid material can circulates through any selective line of the flowing system, thereby enabling the present invention to be also applied as a recycle-type liquid chromatography system in common use.

Besides, the separated-component vessel can function as both a sampler and a fraction collector, and consequently, it is not necessary to additionally provide both apparatus.

What is claimed is:

1. A liquid chromatography system wherein eluent is supplied to a separation column, and a sample of a mixture to be separated is introduced to a flow of the eluent, so that components separated from this sample are individually collected, comprising:

a separation column, a plurality of separated-component vessels for collecting components eluted in the separation column, a first flowing system conduit for conveying components separated in the separation column to the separated-component vessels, a means for selectively drawing components from said vessels, and a second flowing system conduit connected to said means for selectively drawing, said second flowing system conduit for conveying any of the separated samples selectively drawn by said means for selectively drawing to an upstream side of the separation column.

2. The liquid chromatography system according to claim 1, wherein said first flowing system conduit and said second flowing system conduit have a common conduit section.

3. The liquid chromatography system according to claim 2, further including a means for cleaning said common conduit section connected to said common conduit section.

4. A liquid chromatography system wherein eluent is supplied to a separation column, and a sample of a mixture to be separated is introduced to a flow of the eluent, so that components separated from this sample are individually collected, comprising:

a separation column,
a plurality of separated-component vessels for collecting components eluted in the separation column,
a sample injection chamber connected between an eluent supplying pump and the separation column,
a nozzle selectively inserted into the separated-component vessels, and
a means for operating the nozzle such that any separated components collected in said plurality of separated-component vessels is selectively drawn through the nozzle from its vessel and introduced into the sample injection chamber.

5. The liquid chromatography system according to claim 4, wherein said means for operating the nozzle is automatically actuated.

6. The liquid chromatography system according to claim 4, further including a connecting means for connecting said nozzle with a downstream side of said separation column such that said nozzle deposits components separated in said separation column into said separated-component vessels.

7. The liquid chromatography system according to claim 6, wherein said connecting means includes a valve for disconnecting a conduit at the downstream side of said separation column from the nozzle and connecting a drain.

8. A liquid chromatography system wherein eluent is supplied to a separation column, and a sample of a mixture to be separated by elution is introduced to a flow of the eluent, so that components separated from the sample are individually collected, comprising:

a separation column,
a plurality of separated-component vessels for collecting the components eluted in the separation column,
a plurality of channels respectively associated with the separated-component vessels for delivering therethrough components eluted in the separation column,
means for selecting any of said plurality of channels,
means for conveying separated components collected in an associated separated-component vessel through a selected channel into a flow of the eluent, and
means for supplying the flow of eluent containing separated components into the separation column.

9. The liquid chromatography system according to claim 8, further including a sample introducing valve means located between an eluent supplying pump and said separation column, said valve means comprising a port for receiving a sample injection from a means external to the chromatography system.

10. The liquid chromatography system according to claim 8, wherein said plurality of channels are provided with respective opening and closing valves for selectively opening and closing the respective channels.

11. The liquid chromatography system according to claim 8, further including a connecting member for selectively connecting a downstream side of said separation column to a flowing system conduit connected to said plurality of channels and a drain.

12. A method of utilizing a liquid chromatography system comprising the steps of:
introducing a sample to a separation column;
collecting components separated in the separation column via a common conduit section into a corresponding plurality of separated-component vessels;
cleaning the common conduit section;
selectively drawing the components from a separated-component vessel through the cleaned common conduit section; and
introducing said selectively drawn components into the separation column.

13. A liquid chromatography system, comprising:
separation means for separating samples into components;
means for injecting a starting sample into said separation means;
a plurality of means for storing separated components separated by said separating means;
means for conveying components separated by said separation means into at least one of said plurality of means for storing separated components;
means for selectively drawing the components in any of said means for storing; and
means for injecting the drawn components into said separation means.

14. A liquid chromatography system according to claim 13, wherein said plurality of means for storing separated components are vessels each having a bottom, side walls, and an open top.

15. A liquid chromatography system according to claim 13, further comprising:
detector means for detecting separated components and generating a detection signal when separated components are detected; and
control means for inputting said detection signal and controlling said means for selectively drawing and said means for injecting according to said detection signal.

16. A liquid chromatography system according to claim 13, further comprising:
a conduit which is common to both said means for conveying separated components and said means for selectively drawing, and
cleaning means for cleaning said common conduit after said common conduit conveys components into said separation means and before said separated components are selectively drawn and injected into said separation means.

17. A method for controlling a liquid chromatography system, comprising the steps of:
injecting a starting sample into a separation means;
separating the sample in said separation means;
conveying components which have been separated in said separation means into a plurality of means for storing separated components;
selectively drawing said separated components from said means for storing said separated components;
injecting into said separation means said selectively drawn components; and
re-separating said injected selectively drawn components in said separation means.

18. A method for controlling a liquid chromatography system according to claim 17, further comprising the step of conveying said re-separated components into said means for storing separated components.

* * * * *